(12) United States Patent
Dudek

(10) Patent No.: US 10,386,260 B2
(45) Date of Patent: Aug. 20, 2019

(54) LEAK DETECTION FOR FLUID DISTRIBUTION NETWORKS USING HYPERSPECTRAL IMAGING

(71) Applicant: Accenture Global Solutions Limited, Dublin (IE)

(72) Inventor: Marian Dudek, Houston, TX (US)

(73) Assignee: Accenture Global Solutions Limited, Dublin (IE)

( * ) Notice: Subject to any disclaimer, the term of this patent is extended or adjusted under 35 U.S.C. 154(b) by 276 days.

(21) Appl. No.: 15/452,221

(22) Filed: Mar. 7, 2017

(65) Prior Publication Data

US 2018/0259418 A1 Sep. 13, 2018

(51) Int. Cl.
| | |
|---|---|
| *G01M 3/04* | (2006.01) |
| *G01N 33/00* | (2006.01) |
| *G06T 7/00* | (2017.01) |
| *G01M 3/38* | (2006.01) |
| *G01N 21/31* | (2006.01) |
| *H04N 7/18* | (2006.01) |
| *G01M 17/007* | (2006.01) |
| *G01N 21/17* | (2006.01) |

(52) U.S. Cl.
CPC ............. *G01M 3/04* (2013.01); *G01M 3/38* (2013.01); *G01M 17/007* (2013.01); *G01N 21/31* (2013.01); *G01N 33/004* (2013.01); *G01N 33/0047* (2013.01); *G06T 7/0004* (2013.01); *H04N 7/188* (2013.01); *G01N 2021/1793* (2013.01); *G06T 2207/30108* (2013.01)

(58) Field of Classification Search
CPC ........ G01M 3/04; G01M 17/007; G01M 3/38; H04N 7/188; G01N 21/31; G01N 33/0047; G01N 33/004; G01N 2021/1793; G06T 7/0004; G06T 2207/30108

USPC .......................................................... 73/40.7
See application file for complete search history.

(56) References Cited

U.S. PATENT DOCUMENTS

| | | | |
|---|---|---|---|
| 9,234,618 B1 | 1/2016 | Zhu et al. | |
| 2014/0002639 A1* | 1/2014 | Cheben ................. | G08B 21/14 348/135 |

(Continued)

FOREIGN PATENT DOCUMENTS

CN 204990697 1/2016

OTHER PUBLICATIONS

European Search Report in European Application 18154754.8, dated Jul. 26, 2018, 12 pages.

(Continued)

*Primary Examiner* — Marrit Eyassu
(74) *Attorney, Agent, or Firm* — Fish & Richardson P.C.

(57) ABSTRACT

Implementations are directed to detecting a fluid leak by performing operations including: capturing, by one or more digital cameras, at least one image, the one or more digital cameras being included in an imaging system attached to a vehicle moving between geographical locations, and the at least one image corresponding to a geographical location, generating, by one or more fluid detectors, spectral data indicative of at least one fluid at the geographical location, receiving from the one or more digital cameras the at least one image, and from the one or more fluid detectors, the spectral data of the fluid at the geographical location, and providing an output signal based on the at least one image and the spectral data, the output signal indicating a fluid leak.

18 Claims, 4 Drawing Sheets

(56) References Cited

U.S. PATENT DOCUMENTS

| | | | | |
|---|---|---|---|---|
| 2015/0185592 A1* | 7/2015 | Eineren | ................ | G03B 17/02 |
| | | | | 348/375 |
| 2015/0323449 A1* | 11/2015 | Jones | ................ | G01N 21/3103 |
| | | | | 356/437 |
| 2016/0214715 A1* | 7/2016 | Meffert | ................ | B64C 39/024 |
| 2017/0336281 A1* | 11/2017 | Waxman | ................ | G01M 3/38 |
| 2018/0172544 A1* | 6/2018 | MacMullin | ................ | G01F 1/00 |
| 2019/0003984 A1* | 1/2019 | Kester | ................ | G01J 5/0066 |

OTHER PUBLICATIONS

European Search Report in European Application 18154754.8, dated Oct. 30, 2018, 11 pages.

* cited by examiner

LEAK DETECTION FOR FLUID DISTRIBUTION NETWORKS USING HYPERSPECTRAL IMAGING

BACKGROUND

Fluid leak detection and repair is a common problem in commercial applications where various fluids are processed, stored, distributed, and utilized. In the petrochemical industry, leak detection devices include so-called sniffer devices. Sniffer devices are configured to identify a petrochemical leak by analyzing the absorption of infrared radiation by a leaking compound at one or more predetermined infrared absorption bandwidths. In particular, sniffer devices are configured to draw a gas sample into a chamber through a probe and to analyze the gas sample by using an infrared radiation beam. One problem associated with the use of sniffer devices in gas leak detection is that the probe must be located within the leak plume itself to directly absorb a gas sample from the leak plume. Accordingly, in a large facility or along large areas including multiple potential fluid leak points, the use of sniffer devices to detect fluid leaks is often unpractical and unreliable. Moreover, in the case of a person carrying a sniffer device through the leak plume, the person can be exposed to health risks.

SUMMARY

Implementations of the present disclosure are generally directed to detecting fluid leaks in fluid distribution networks. More particularly, implementations of the present disclosure are directed to vehicle-based hyperspectral imaging for detecting fluid leaks in fluid distribution networks.

In some implementations, actions include capturing, by one or more digital cameras, at least one image, the one or more digital cameras being included in an imaging system attached to a vehicle moving between geographical locations, and the at least one image corresponding to a geographical location, generating, by one or more fluid detectors, spectral data indicative of at least one fluid at the geographical location, receiving from the one or more digital cameras the at least one image, and from the one or more fluid detectors, the spectral data of the fluid at the geographical location, and providing an output signal based on the at least one image and the spectral data, the output signal indicating a fluid leak. Other implementations of this aspect include corresponding systems, apparatus, and computer programs, configured to perform the actions of the methods, encoded on computer storage devices.

These and other implementations can each optionally include one or more of the following features. The output signal can include a location of the fluid leak. The location of the fluid leak can include the geographical location, a distance between the vehicle and the fluid leak determined based on at least a first portion of the at least one image and at least a second portion of the spectral data, and an orientation. The output signal can indicate an amount of the fluid relative to the geographical location. The amount of fluid can be compared to a set amount. The at least one image and the spectral data can be concurrently captured at the geographical location. The one or more digital cameras and the one or more fluid detectors are rotatable about one or more of a vertical axis and a horizontal axis. The geographical location can include geographical coordinates that are determined by at least one of an accelerometer, a gyroscope, a magnetometer, and a global positioning system sensor. The fluid can include a gas. The fluid can include at least one of hydrocarbons and organic compounds. The hydrocarbon can include at least one of a carbon dioxide, a methane, and an ethylene. The optical beam can include one or more optical wavelengths. The at least one image and the spectral data can be transmitted from the vehicle to a remote device configured to generate the output signal. The one or more fluid detectors can include a hyperspectral camera.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more digital cameras, one or more fluid detectors, one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF DRAWINGS

Like reference symbols in the various drawings indicate like elements.

DETAILED DESCRIPTION

Figure 1:
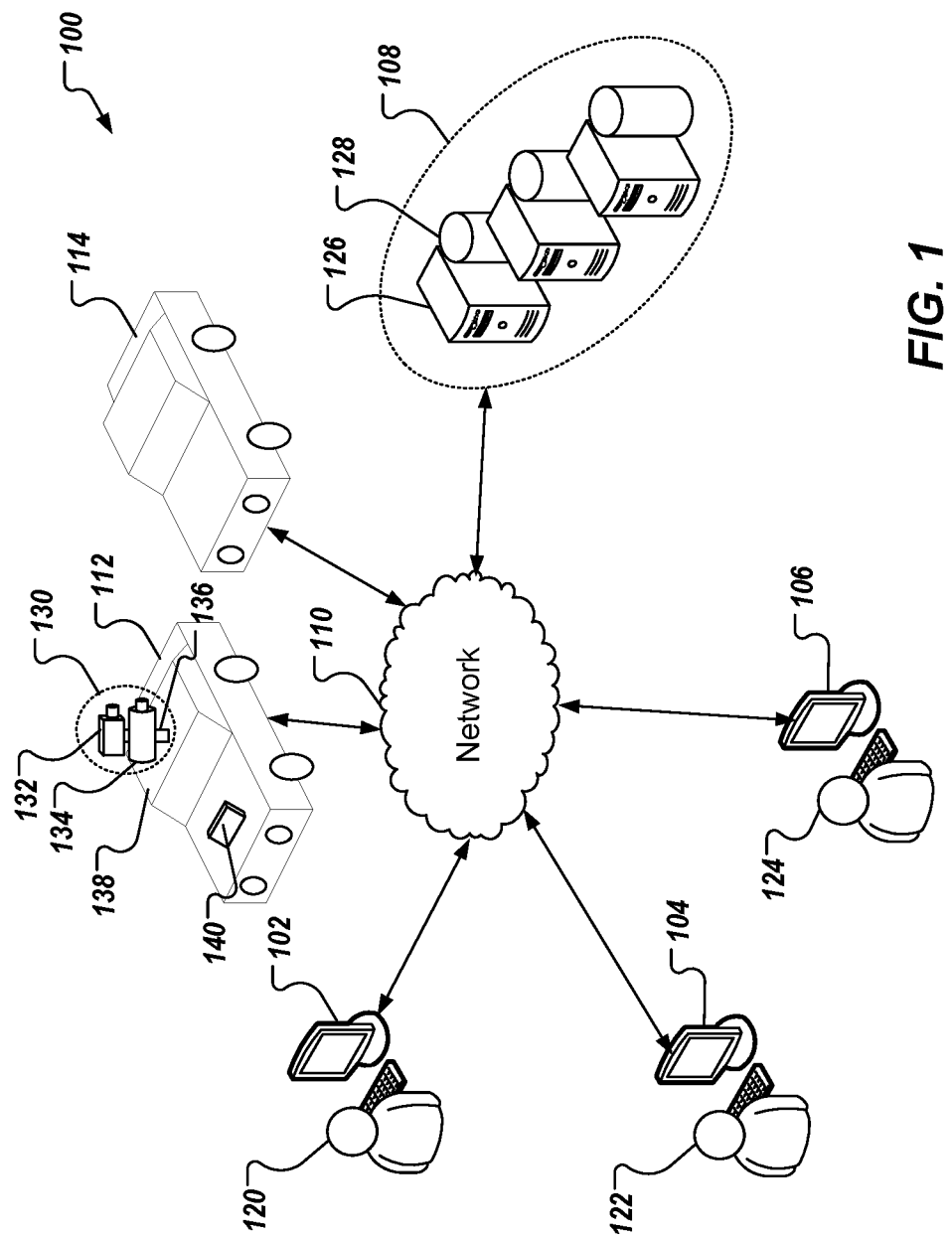
FIG. 1 depicts an example high-level architecture in accordance with implementations of the present disclosure.

Implementations of the present disclosure are generally directed to detecting fluid leaks. More particularly, implementations of the present disclosure are directed to vehicle-based hyperspectral imaging for detecting fluid leaks in large areas. As described in further detail herein, implementations of the present disclosure include capturing, by one or more digital cameras, at least one image, the one or more digital cameras being included in an imaging system attached to a vehicle moving between geographical locations, and the at least one image corresponding to a geographical location, generating, by one or more fluid detectors, spectral data indicative of at least one fluid at the geographical location, receiving from the one or more digital cameras the at least one image, and from the one or more fluid detectors, the spectral data of the fluid at the geographical location, and providing an output signal based on the at least one image and the spectral data, the output signal indicating a fluid leak.

A challenge in fluid leak detection is that a detector, such as a sniffer device, has to be in direct contact with the fluid (e.g., within a gas plume) to detect and identify the fluid leak. Accordingly, use of a sniffer device can be impractical, because access to a leak may be hindered. For example, in the case of vehicle-mounted sniffer devices, the vehicle would have to travel through a plume, but the plume may be in a location that is inaccessible to the vehicle. In the case of person-carried sniffer devices, the person would have to pass through the plume, which may expose the person to hazards.

As described in further detail herein, implementations of the present disclosure address this challenge. For example, in accordance with implementations, images captured by a digital camera attached to a vehicle in motion are combined with spectral data (e.g., hyperspectral images) generated by a fluid detector that is also attached to the vehicle to identify a fluid leak that is remote from the vehicle.

In accordance with implementations of the present disclosure, fluid leaks directly affecting people and/or the environment can be quickly and efficiently mitigated. For example, to diminish the impact of the fluid leaks on the environment, implementations of the present disclosure quickly and efficiently provide spectral data to determine relevant information that can be automatically processed to react quickly to the occurrence of fluid leaks, assess the impact, determine the appropriate remedial actions, and implement the remedial actions.

Implementations of the present disclosure will be described in further detail herein with reference to an example context. Within the example context, the fluid includes natural gas leaks in gas distribution networks (e.g., in densely populated residential areas), a chemical spill (e.g., in the proximity of a factory or chemical plant), or an oil spill (e.g., in the vicinity of a slurry transmission pipeline). For example, implementations of the present disclosure can be used to determine hydrocarbons or organic compound leaks, including carbon dioxide, methane, and/or ethylene. It is contemplated, however, the implementations of the present disclosure can be realized in any appropriate context.

FIG. 1 depicts an example system 100 that can execute implementations of the present disclosure. The example system 100 includes computing devices 102, 104, 106, a back-end system 108, a network 110, a detection vehicle 112, and a work crew vehicle 114. The computing devices 102, 104, 106, the back-end system 108, the vehicle 112, and the work crew vehicle 114 can communicate over the network 110. In some implementations, the network 110 includes a local area network (LAN), wide area network (WAN), the Internet, or a combination thereof, and connects web sites, devices (e.g., the computing device 102, 104, 106), and back-end systems (e.g., the back-end system 108). In some implementations, the network 110 can be accessed over a wired and/or a wireless communications link. For example, mobile computing devices, such as smartphones can utilize a cellular network to access the network 110.

In the depicted example, the back-end system 108 includes at least one server system 126, and data store 128 (e.g., database). In some implementations, one or more components of the back-end system 108 may be configured to operate within environments, including cloud-computing-based, local, global, or other environment (or a combination of environments). The at least one server system 126 can host one or more computer-implemented services that users can interact with using computing devices 102, 104, 106. For example, the server system 126 can host a computer-implemented service or a set of cloud services for identifying fluid leaks in accordance with implementations of the present disclosure. The set of cloud services can be accessible over one or more networks (for example, the Internet) by the server system 126. The cloud services include services designed for identifying fluid leaks and social network platforms (for example, TWITTER®, FACEBOOK®, GOOGLE+®). The cloud services 102 can include other social network platforms (for example, blogs), and other types of cloud services (for example, a weather data service, a news service, or any other type of service).

The computing device 102 can be operated by a user 120, the computing device 104 can be operated by a user 122, and the computing device 104 can be operated by a user 124. In some implementations, the computing devices 102, 104, 106 can each include any appropriate type of computing device such as a desktop computer, a laptop computer, a handheld computer, a tablet computer, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices or other data processing devices.

The vehicle 112 can be a self-driven vehicle, private cars and/or trucks, as well as operations vehicles. Operations vehicles can include vehicles that are used by a facility (e.g., a federal, state, or local government; a private enterprise). In some implementations, vehicles can be primarily configured to perform fluid leak detection operations (e.g., a particular trajectory is selected for the vehicle to verify fluid leak in a particular area). In some implementations, vehicles can be secondary configured to perform fluid leak detection operations (e.g., the travel path of the vehicle is selected according to an operation that is independent from the fluid leak detection process). For example, vehicles can include company vehicles used by employees of the enterprise (e.g., sales-persons who use the vehicles to visit customers), or vehicles can include cars and/or trucks used in the supply chain of an enterprise. The company vehicles can be configured to perform fluid leak detection operations continuously, during each trip, independent of the travel path.

The vehicle 112 can include a detection system 130. The detection system 130 includes a digital camera 132 and a fluid detector 134. In some implementations, the detection system 130 is configured such that the digital camera 132 and the fluid detector 134 are oriented in the same direction (e.g., having overlapping fields of view). For example, the digital camera 132 and the fluid detector 134 can be coaxial to each other and oriented at an angle to correct for the height difference such that the digital camera 132 and the fluid detector 134 have overlapping focal points, or fields of view. The digital camera 132 can be any camera capable of taking still pictures in visible spectrum (e.g., two-dimensional digital images), or moving pictures in visible spectrum (e.g., videos) of any objects and surroundings external to the vehicle 112 (e.g., buildings, vegetation, pipelines, traffic lights, street signs, store names, etc.). The digital camera 132 can be configured to be rotatable with 360 degrees around a vertical axis 136. The digital camera 132 can be configured to tilt with 90 degrees relative to a horizontal plane 138 to adjust a position of a focal point of the camera. The digital camera 132 can be configured to determine its orientation (e.g., based on the angles relative to the vertical axis 136 and the horizontal plane 138). In some implementations, a focal distance of the digital camera 132 can be adjusted to vary within a range (e.g., between approximately 1 meter and 10 meters). In some implementations, the lens of the digital camera 132 can be focused at infinity to extend the lens focal length to the horizon line. The digital camera 132 can include wide angle lens (e.g., 10-24 mm) and can have a variable or a fixed angle of view, such that the width of the captured image can be between, for example, 1 meter and 10 meters (e.g., 6 meters).

The fluid detector 134 can be an active remote sensing system, or a hyperspectral imaging system. The fluid detector 134 can include a transmitter (e.g., an illumination source) and a receiver. In some implementations, the sun can be used as the illumination source, and the daytime illumination can include scattered solar (skylight), which is caused by the presence of the atmosphere. In some implementations, the illumination source is a broadband light source configured to generate a light beam (e.g., a laser beam) of a broadened spectrum including wavelengths between, for example, approximately 350 nanometers and 2500 nanometers. In some implementations, the illumination source is limited to the short-wave infrared spectrum, such that the illumination source operates in the so-called "eye safe" window, which corresponds to wavelengths longer than approximately 1400 nanometers. Since wavelengths longer than about 1400 nanometers are substantially not transmitted to the retina or substantially absorbed in the retina, this wavelength range is known as the "eye safe" window referenced above. For wavelengths longer than 1400 nanometers, in general, only the cornea of the eye can receive or absorb the light radiation. In some implementations, the range of the illumination source is determined based on a location of the vehicle 112, such that in inhabited areas (e.g., within city limits) the range is limited to the "eye safe" window and in non-inhabited areas (e.g., along pipelines) the range can be extended to entire near infrared spectrum.

The receiver of the fluid detector 134 is configured to receive at least a portion of the light beam that intersected and/or was reflected by fluids within a target area (e.g., located 1 meter to 200 meters away from the fluid detector 134). The receiver can have a bandwidth of at least 10 nanometers, for example. The receiver is configured to process the portion of the light beam to generate spectral data. The spectral data correspond to the absorbance as a function of light frequency for each fluid within the target area (e.g., optical field of the receiver). The spectral data generated by the fluid detector 134 can quantitatively correspond to a designated column density of a fluid in units, such as ppm-m or $g/m^2$, for example. For example, each pixel of the spectral data can include a spectrum vector k that can be associated to a quantity of fluid within the target area.

The fluid detector 134 can be configured to be rotatable with 360 degrees around a vertical axis 136. The fluid detector 134 can be configured to tilt with 90 degrees relative to a horizontal plane 138 to adjust a position of the target area to match the images captured by the digital camera 132. The fluid detector 134 can be configured to determine its orientation (e.g., based on the angles relative to the vertical axis 136 and the horizontal plane 138). In some implementations, the orientation of the fluid detector 134 is aligned with an orientation of the digital camera 132, such that the fluid detector 134 is configured to modify its orientation based on a modification of the orientation of the digital camera 132.

The digital camera 132 and the fluid detector 134 can be synchronized to simultaneously capture the digital images and the corresponding spectral data at a particular framerate. The framerate can be selected and adjusted based on the velocity of the vehicle 112. For example, the framerate can be selected such that an area around the vehicle is continuously analyzed (e.g., without spatial gaps) to enable a reconstruction of a three-dimensional volume along the displacement path of the vehicle 112. In some implementations, the detection system 130 can be configured to transmit the digital images and the corresponding spectral data to the data collection system 140.

In some implementations, the data collection system 140 includes one or more sensors that are responsive to the operation of the vehicle 112. In some implementations, data collection system 140 can include components that are already provided with the vehicle 112 to provide functionality described herein. In some implementations, data collection systems 140 can include special-purpose components that are integrated into the vehicle 112 to provide functionality described herein. The data collection system 140 can be responsive to, and can record ambient data (e.g., vehicle location data, vehicle orientation data, operational data, meteorological data, etc.). Vehicle location data can include geographical coordinates that can be determined by at least one of an accelerometer, a gyroscope, a magnetometer, and a global positioning system (GPS). Vehicle location data can be used to determine a location of the vehicle, the route that the vehicle traveled, and/or a velocity and acceleration history of the vehicle, among other information. Operational data can include velocity, acceleration, braking, engine data, transmission data and the like.

In some implementations, the data collection system 140 can directly communicate ambient data and fluid detection data received from the detection system 130 (e.g., digital images, corresponding spectral data, and orientation of the detection system) to the backend system 108 over the network 110, for example. In some implementations, the data collection system 140 can transmit ambient data and fluid detection data to one or more intermediate computing devices 102, 104, 106, for example, and the one or more intermediate computing devices 102, 104, 106 can transmit the ambient data and fluid detection data to the backend system 108 over the network 110.

In some implementations, the ambient data is periodically transmitted to the backend system 108. For example, batch ambient data and fluid detection data can be transmitted at pre-defined intervals (e.g., minutely, hourly, daily). In some implementations, ambient data and fluid detection data can be transmitted in real-time over the network 110 to the backend system 108. For example, ambient data and fluid detection data can be continuously transmitted to the back-end system 108 as the data is recorded, while the vehicle 112 travels.

As discussed in further detail herein, the backend system 108 can process the ambient data and the fluid detection data to determine whether a fluid leak is present, and to identify and implement remedial actions in response to the fluid leak. For example, the back-end system 108 can host a leak identification system that can be used to process the ambient data and the fluid detection data to determine the presence and location of a fluid leak. The leak identification system can access the data store 128 to retrieve a list of fluids found in a spectral library. The list of fluids can be a list of chemical names that correspond to a subset of the spectral library. The leak identification system can filter the spectral data using the list of fluids to identify a presence of one or more fluids (e.g., in respective amounts that exceed respective thresholds). The leak identification system can be configured to trigger a notification, when a fluid is detected, or is detected and is in an amount that exceeds a respective threshold. The leak identification system can be configured to process the digital pictures, orientation data, and ambient data to determine a location of the fluid leak. In some implementations, the leak identification system can be configured to determine the location of the fluid leak within a predetermined accuracy (e.g., a few millimeters).

In some implementations, the backend system 108 can conform to a particular fluid leak protocol. In some implementations, the backend system 108 identifies one or more remedial actions based on the fluid leak, the type(s) of fluid(s), and/or the severity of the fluid leak (e.g., volume and concentration of detected fluid). In some implementations, the backend system 108 can coordinate the implementation of remedial actions between entities. For example, the backend system 108 can communicate with an entity (e.g., an internal entity 102 or an external entity 104, 106), and can provide additional data received from the entity to another entity (e.g., an internal entity 102 or an external entity 104, 106). In some implementations, the backend system 108 can notify the internal entity 102 of the fluid leak and determined remedial actions. For example, the internal entity 102 can identify and transmit the fluid leak data to an external entity 104 that could be responsible for the fluid leak. The internal entity 102 can identify and transmit the fluid leak data to an external entity 106 that could perform the determined remedial actions (e.g., send the work crew vehicle 114 to perform a repair and clean the affected area). In some implementations, the backend system 108 can directly contact the external entity 106 according to a set of rules to perform the determined remedial actions (e.g., send the work crew vehicle 114 to perform a repair and clean the affected area).

Although FIG. 1 depicts a single digital camera 132, and a single fluid detector 134, implementations of the present disclosure can include multiple digital cameras 132, and/or multiple fluid detectors 134. For example, a set of digital cameras 132 can be configured to capture images in different directions (e.g., equally dispersed between 180-degrees or 360-degrees relative to the orientation of the vehicle). As another examples, a set of fluid detectors 134 can be configured to capture spectral data in different directions (e.g., equally dispersed between 180-degrees or 360-degrees relative to the orientation of the vehicle). In some implementations, the number of digital cameras 132 in the set of digital cameras 132 matches the number of fluid detectors 134 in the set of fluid detectors 134, and each digital camera 132 in the set of digital cameras 132 is aligned with a corresponding fluid detector 134 in the set of fluid detectors 134.

Figure 2:
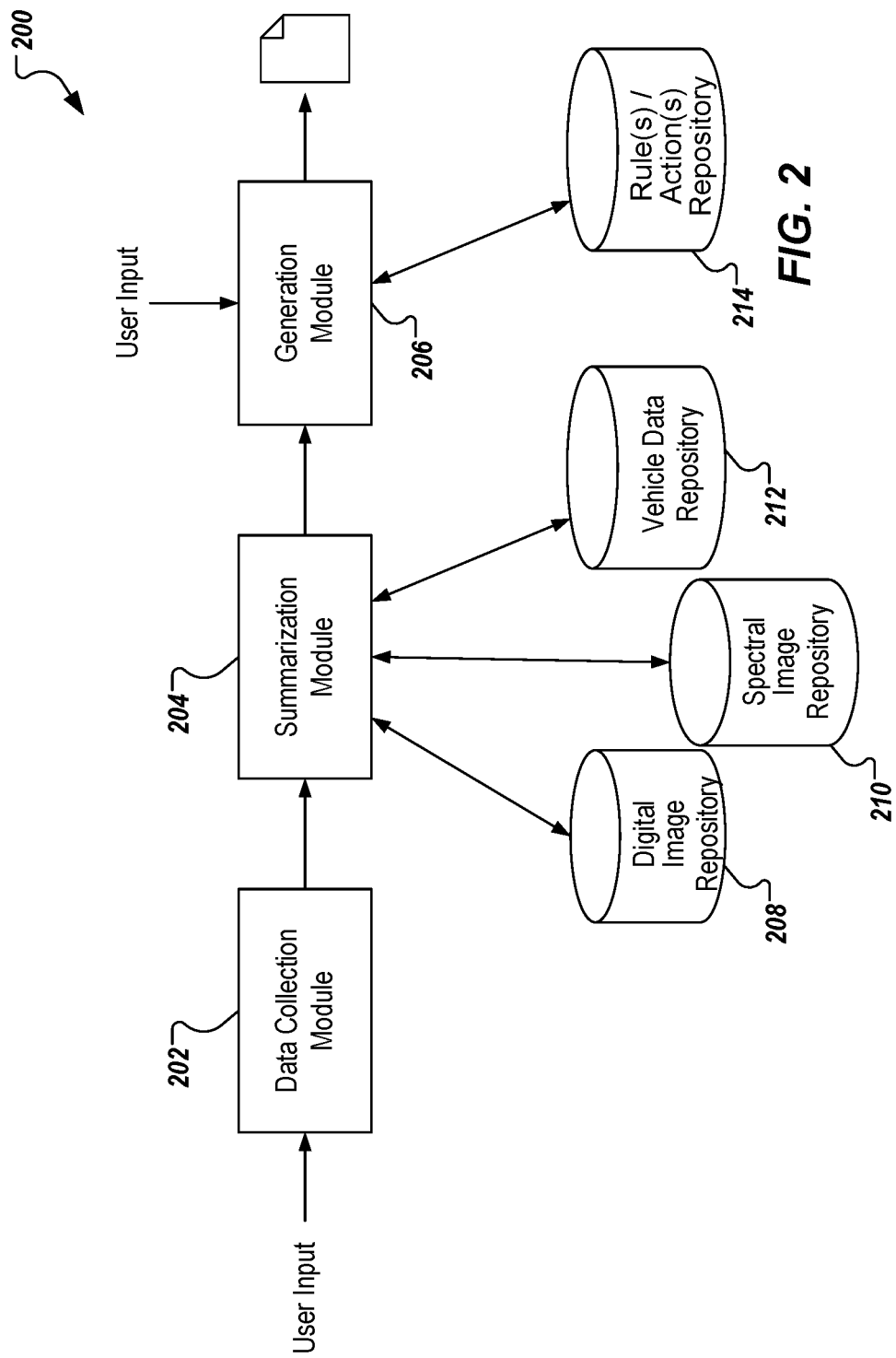
FIG. 2 schematically depicts an example electronic document generation platform in accordance with implementations of the present disclosure.

FIG. 2 schematically depicts an example platform 200 in accordance with implementations of the present disclosure. The example platform 200 includes a data collection module 202, a summarization module 204, and a generation module 206. In some implementations, each of the data collection module 202, the summarization module 204, and the generation module 206 are provided as one or more computer-executable programs that can be executed using one or more computing devices (e.g., in the backend system 108 of FIG. 1).

In some implementations, the data collection module 202 receives a user input indicating that data should be collected and generates a signal defining one or more characteristics of the data collection procedure. The one or more characteristics can include a frame rate, a resolution of the digital images and/or spectral data, and a focal distance. In some implementations, the summarization module 204 can receive and/or provide data to each of the digital image repository 208, the spectral image repository 210, and the ambient data repository 212. The summarization module 204 can process (e.g., match, summarize and/or integrate) the digital images (e.g., images in visible spectrum), the spectral data (e.g., hyperspectral images), and the ambient data to generate summarized data including at least a portion of the digital images, a portion of the spectral data, and a portion of the ambient data.

In some implementations, the generation module 206 can receive summarized data from the summarization module 204, can retrieve one or more sets of rules from a rule or action repository 214, can receive a user input to define a new rule or update an old rule and can generate an output signal indicating a fluid leak threat. In some implementations, the generation module 206 can process the received data to determine whether a fluid leak has been identified. In some implementations, the generation module 206 can receive a rule set from the repository 214. In some implementations, the generation module 206 can process the received data based on the retrieved rules to determine whether a fluid leak has occurred. For example, an example rule can provide that, if one or more spectral data (e.g., hyperspectral images) indicate the existence of a fluid leak, it is determined that a fluid leak has occurred.

In some cases, indication of a fluid leak might not be as explicit. More complex rules can be provided to determine whether a fluid leak has occurred. An example rule can provide that, if digital images indicate localized affected vegetation, and the presence of a hazardous fluid even below standard alert threshold, it is determined that a fluid leak has occurred.

In response to determining that a fluid leak may have occurred, the generation module 206 can communicate with the user to request additional data. For example, the generation module 206 can call the operator of the vehicle (e.g., through a communications device provided with the data collection system, through a mobile device of the operator of the vehicle) to request the generation of a second set of digital data and spectral data. As another example, the generation module 206 can provide instructions to a human employee of the enterprise to contact the operator of the vehicle.

In some implementations, the rule set can be specific to a location type associated with the received data. For example, a first rule set can be associated with inhabited areas (e.g., housing areas with private properties), a second rule set can be associated with industrial areas (e.g., areas including factories, laboratories, farms or other businesses that can use, process, receive, and transport hazardous fluids), and a third rule set can be associated with non-inhabited areas (e.g., areas including pipelines configured to carry fluids therethrough). In some implementations, the type of fluid to be identified and the threshold quantity of fluid to generate a fluid leak alert can vary between the first, the second and the third sets of rules. For example, in inhabited areas, at least one of the fluid types to be identified can be methane. The knowledge related to the fluid types that can be handled in the industrial area can define the fluid types to be searched for in the industrial area. The knowledge related to the fluid types that flow through pipelines can define the fluid types to be searched for along pipelines, in the non-inhabited areas.

In some implementations, if it is determined that a fluid leak has occurred, the summarized data can be further processed to determine a severity of the fluid leak. In some implementations, the generation module 206 processes the summarized data to determine the volume and/or density of the leaking fluid, vehicle location data, immediate and long term associated risks, and other relevant data to determine the severity of the fluid leak. In some implementations, digital images and spectral data can explicitly indicate a severity of the accident. For example, if a digital image indicates the presence of people in the proximity of the fluid leak and the spectral data indicate a large volume of fluid, it can be determined that a severe fluid leak with high risk has occurred.

In some implementations, and in response to determining that a fluid leak has occurred, the generation module 206 can determine one or more remedial actions that are to be performed and can dispatch instructions and data to entities that are tasked with performing the remedial actions. In some implementations, the generation module 206 receives a set of action rules from the repository 214. In some implementations, the summarized data is processed based on the action rules to determine the remedial actions that are to be performed. Example remedial actions can include automatically generating and sending a message to inform an entity associated with the fluid leak (e.g., fluid provider, fluid distributor of fluid source) and providing relevant data, providing emergency response to the location of the fluid leak, dispatching another vehicle to repair the equipment generating the fluid leak, to clean the area affected by the fluid leak and to provide medical assistance to any persons who could have been affected by the fluid leak.

In some implementations, data can be provided by the generation module 206 to assist in execution of the remedial actions. For example, a type and quantity of tools and materials that are to be used for remedying the fluid leak, and cleaning the affected area can be provided. In some implementations, the one or more remedial actions can be determined based on the severity of the fluid leak. For example, if the fluid leak is determined not to be severe, only service vehicles are dispatched to repair the leaking equipment and to prevent future fluid leaks, while emergency responders might not be required. As another example, if the fluid leak is determined to be very severe the actions can include dispatching service vehicles and emergency responders.

Figure 3:
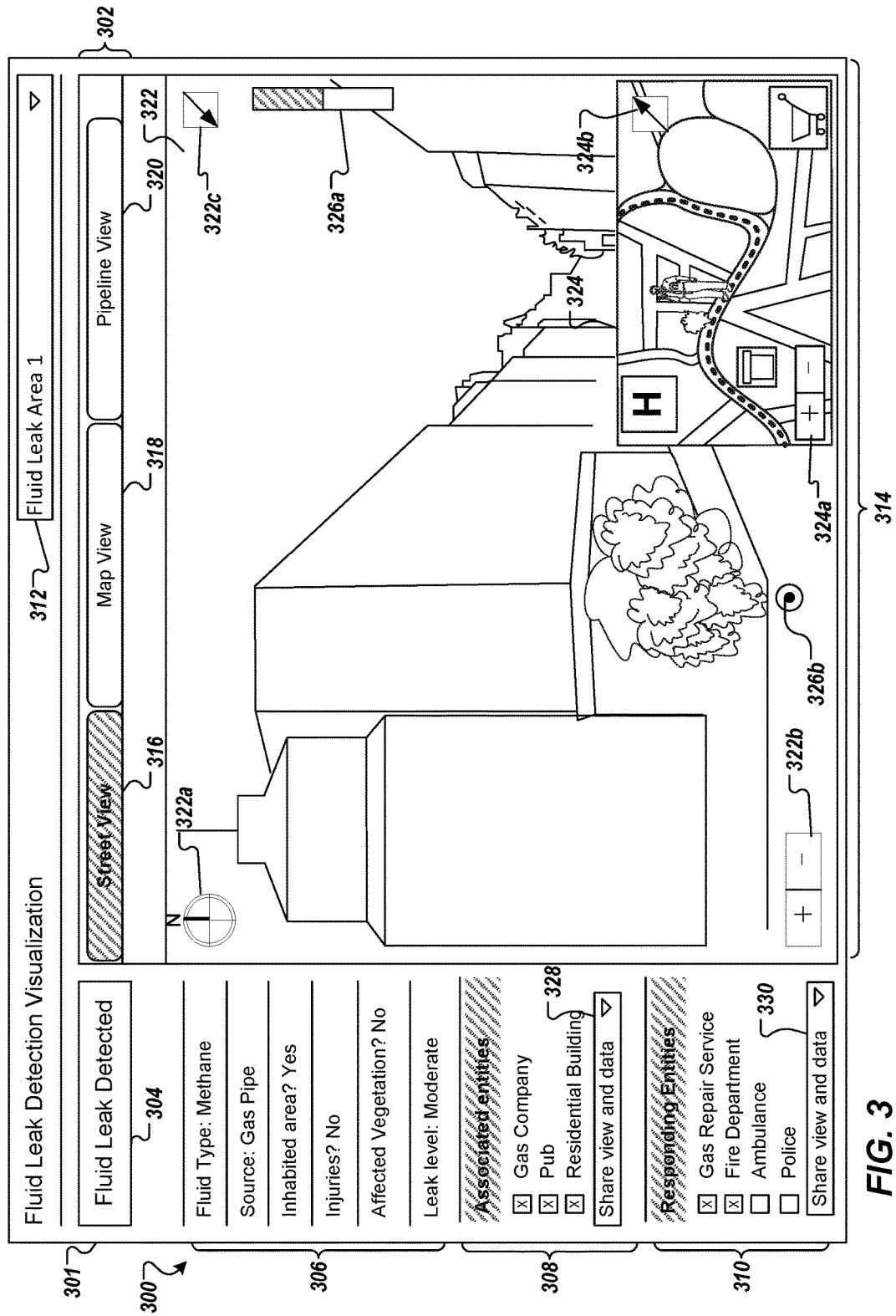
FIG. 3 an example of a graphical user interface in accordance with implementations of the present disclosure.

FIG. 3 depicts a screen-shot 300 of an example graphical user interface for viewing a fluid leak detection. The screen-shot 300 can be displayed to a user, for example a worker, who is sent to locate and/or repair a fluid leak. In the screen-shot 300, a fluid leak detection visualization user interface (UI) 301 is shown. In some implementations, the UI 301 can be the interface presented by a purpose made fluid detection application, while in some implementations the UI 302 can be one or more web pages of a fluid detection website displayed in a general purpose web browser.

In the example of FIG. 3, the UI 301 includes a number of visualization choices presented in a menu bar 302, an alert box 304, a fluid leak data menu 306, an associated entities menu 308, a responding entities menu 310, a menu of fluid leak areas 312, and a display 314. The associated entities menu 308 can include a selection of one or more entities associated with the fluid leak, including a fluid provider (e.g., gas company), a commercial entity (e.g., hotel, factory, store, restaurant, pub, bakery, etc.), and residential building (e.g., block of flats, duplex, house). In some implementations, the associated entities menu 308 lists generic names (e.g., natural gas company) of the associated entities or the specific names (e.g., Gazprom®) of the associated entities. For example, the generic or specific names of the associated entities can be determined based on the location of the fluid leak and can be displayed within the associated entities menu 308. The responding entities menu 310 can include a selection of one or more entities that are configured to provide remedial service in response to the fluid leak, including a gas repair service, a fire department unit, a healthcare provider and police. The responding entities menu 310 can list generic or specific names of the responding entities menu 310 that can be determined for display based on the location of the fluid leak.

The menu of fluid leak areas 312 can be a drop down menu, that can be configured to enable a user to navigate between multiple areas, where fluid leak was detected. The menu bar 302 includes a "Street View" option 316, a "Map View" option 318, and "Pipeline View" option 320. The display 314 includes a global section 322, a corner section 324, a fluid leak bar 326a and a fluid leak location marker 326b. In some implementations, the data displayed in the alert box 304, the fluid leak data menu 306, and the display 314 can be automatically filled in response to a detection of a fluid leak or in response to a selection from the menu of fluid leak areas 312. The selections within the associated entities menu 308 and the selections within the responding entities menu 310 can be automatically set in response to a detection of a fluid leak or in response to a selection from the menu of fluid leak areas 312.

In the present example, the "Fluid Leak Area 1" and the "Street View" option 316 have been selected by a user. This selection causes a fluid detection application to be executed and an image captured by a digital camera overlapped by a spectral image to be displayed in the global section 322 of the display 314 and a corresponding map image to be displayed in the corner section 324 of the display 314. The fluid leak bar 326a can illustrate the severity of the fluid leak. For example, a filled fluid leak bar 326a can indicate a severe fluid leak, a partly (e.g., half) filled fluid leak bar 326a can indicate a moderate fluid leak, and a minimally (e.g., less than 10%) filled fluid leak bar 326a can indicate a minor fluid leak.

A user can interact with the global section 322 of the display 314 and/or the corner section 324 of the display 314 to modify the display by changing the orientation of the display (e.g., by interacting with the compass 322a) or by selecting a zooming option (e.g., by interacting with zooming element 322b, 324a). A user can interact with an element 322c of the global section 322 and/or an element 324b of the corner section 324 to interchange the views of the area with the fluid leak. A user can interact with the global section 322 and/or the corner section 324 (e.g., by selecting and dragging the image in a particular direction) to navigate between different locations of fluid leak detection. A user can share a displayed view and/or fluid leak data with one or more entities by selecting one or more entities in the associated entities menu 308 and/or one or more entities in the responding entities menu 310 and selecting the share buttons 328, 330. As describer in further detail, with reference to FIG. 4, the screen-shot 300 of the example graphical user interface can be shared with one or more entities to assist with a repair of the detected fluid leak.

Figure 4:
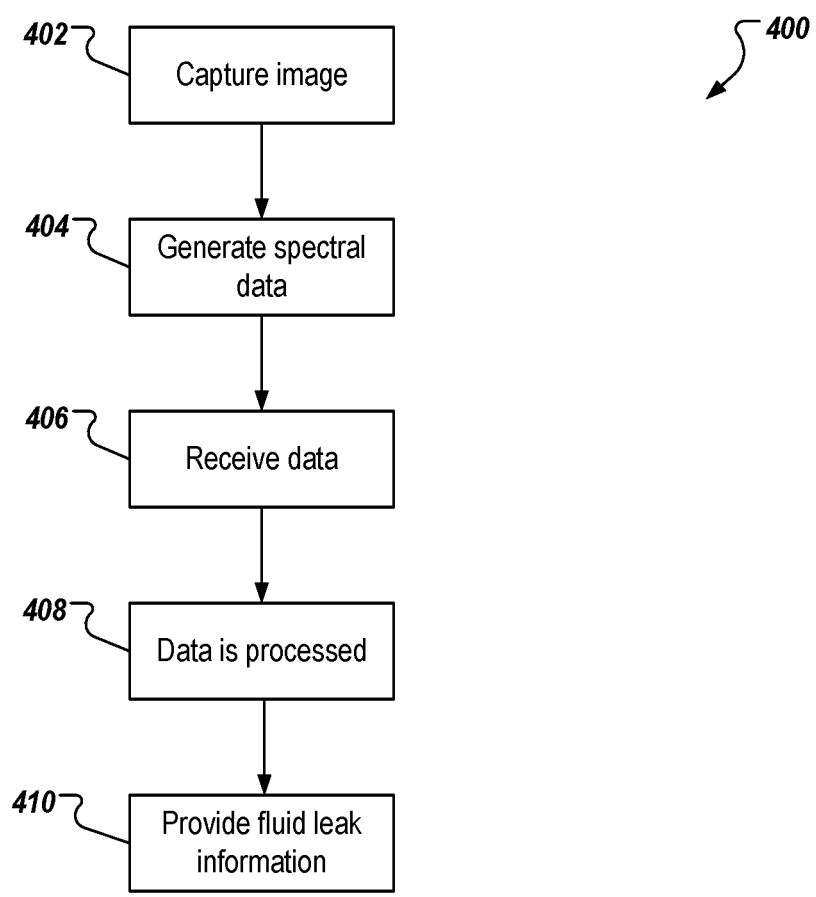
FIG. 4 is a flowchart depicting an example process that can be executed in accordance with implementations of the present disclosure.

FIG. 4 depicts an example process 400 that can be executed in implementations of the present disclosure. In some implementations, the example process 400 is provided using one or more computer-executable programs executed by one or more computing devices (e.g., the back-end system 108 of FIG. 1). The example process 400 can be executed to detect a fluid leak in accordance with implementations of the present disclosure. In some implementations, the example process 400 is initiated in response to a user input defining one or more parameters for capturing images and spectral data. In some implementations, the example process 400 is initiated automatically in response to detecting that a detection vehicle equipped with a fluid detection system (e.g., including a digital camera and a fluid detector) is moving between multiple geographical locations.

Images are captured in visible spectrum (402). For example, a set of images are captured by a digital camera attached to a vehicle that moves along a path including multiple geographical locations. In some implementations, at least one image is captured at each geographical location. For example, at each location the digital camera can be configured to capture one picture in a direction parallel or perpendicular to the orientation of the vehicle. As another example, at each location the digital camera can be configured to capture multiple pictures forming a 180-degree or 360-degree view relative to the orientation of the vehicle. In some implementations, at each location the multiple digital cameras are can be configured to capture images in different directions (e.g., equally dispersed between 180-degrees or 360-degrees relative to the orientation of the vehicle). In some implementations, the framerate to capture the images can be set based on one or more parameters, such as the velocity of the vehicle, the number of pictures per geographical location, and the aperture of the camera.

Spectral data (e.g., hyperspectral images) are generated (404). The spectral data can be generated by a fluid detector attached to the same vehicle as the digital camera. In some implementations, generating spectral data includes generating a light beam, capturing a spectral signal and converting the spectral signal to hyperspectral images. The light beam can be generated using an illumination source configured to generate a light beam (e.g., a laser beam) of a broadened spectrum. The broadened spectrum can include wavelengths from approximately 350 nanometers to approximately 2500 nanometers (e.g., entire near infrared spectrum) or from approximately 1400 nanometers to approximately 2500 nanometers (e.g., "eye safe" window). In some implementations, the range of the illumination source is selected based on a location of the vehicle 112, such that in inhabited areas (e.g., within city limits) the range is from approximately 1400 nanometers to approximately 2500 nanometers and in non-inhabited areas (e.g., along pipelines) the range can be extended to entire near infrared spectrum.

The spectral signal is received by a receiver included in the fluid detector that is configured to receive at least a portion of the light beam that intersected and/or was reflected by fluids. The spectral signal can be processed by the fluid detector to generate hyperspectral images. The hyperspectral images correspond to the absorbance as a function of light frequency for each fluid within the target area. The hyperspectral images generated by the fluid detector can quantitatively correspond to the concentration and location of fluids within the spectroscopically analyzed area.

In some implementations, the spectroscopically analyzed area associated to the hyperspectral images substantially matches the optical field of the captured images. For example, the orientation of the fluid detector can be aligned with an orientation of the digital camera, such that any modification of the optical field of the digital camera is substantially instantaneously followed by a matching modification of the spectroscopically analyzed area. In some implementations, the images captured by the digital camera and the hyperspectral images include a reference feature that can enable pre-processing and/or post processing spatial alignment of the images captured in the visible spectrum with the hyperspectral images.

In some implementations, the hyperspectral images are captured simultaneous to the visible spectrum images. For example, the digital camera and the fluid detector can be synchronized to simultaneously capture the digital images and the corresponding hyperspectral images at a particular framerate. The framerate can be selected and adjusted based on the velocity of the detection vehicle. For example, the framerate can be selected such that an area around the vehicle is continuously analyzed (e.g., without spatial gaps) to enable a reconstruction of a three-dimensional volume along the displacement path of the detection vehicle.

Data is received by one or more processors (406). In some implementations, the received data includes the visible spectrum images, the corresponding hyperspectral images, pipeline topology, and ambient data that was recorded simultaneously with the images captured by the camera and the hyperspectral images. Pipeline topology can be received, from an external database (e.g., from a database of a gas distribution entity that provides natural gas in an area where a fluid leak was identified). Ambient data can include vehicle location data, vehicle orientation data, operational data, and meteorological data. Vehicle location data can include GPS data that can be used to determine a location of the vehicle, the route that the vehicle traveled, and/or a velocity and acceleration history of the vehicle among other information. Operational data can include velocity, acceleration, braking, engine data, transmission data and the like.

Data is processed (408). In some implementations data processing can include data filtering, object detection, data matching, and extraction of fluid leak location, quantity, and volume. Data filtering can include image filtering. Image filtering can include removal of background noise and/or optical targets according to one or more rules (e.g., removal of particular physical features of people to conform to privacy rules). Data filtering can include spectral image filtering. Spectral image filtering can include removal of background noise and/or presence of fluids according to one or more rules (e.g., removal of non-hazardous fluids). Spectral image filtering can include retrieving a threat list of threat fluids from a spectral library. The threat fluid list can be a list of chemical names that correspond to a subset of the spectral library. Spectral image filtering can include using the threat fluid list to identify threat fluids that exceed a particular threshold per pixel. Object detection can include any image processing method configured to extract an object and/or a background of an image. An image can be segmented into two or more segments, each segment corresponding to an object type (e.g., building, gas pipe, street sign, tree, grass, floral area, human, animal, etc.). Object detection can include processing each segment, to perform a color correction based on depth variation and environmental associated shading (e.g., presence of clouds) and determining affected objects. The affected objects can be determined based on a condition of the objects (e.g., a dead tree, dead grass, etc.) as indicated by an anomaly in color (e.g., yellow grass) or anomaly in shape (e.g., leafless tree).

Data matching can include overlapping of filtered visible spectrum images with filtered hyperspectral images, pipeline topology, and automatically matching a location of a fluid leak with one or more objects within the images (e.g., a pipeline, a fluid tank, dead vegetation, etc.). The extraction of fluid leak location, quantity, and volume can include multiple techniques that determine the position of the fluid leak and/or a matching object relative to the location of the camera, the fluid detector, and/or the vehicle. The extraction techniques can include geometric calculations based on triangulation of multiple images, stereoscopic images, focal-length techniques, etc. The extraction techniques can include a laser rangefinder for laser detection and ranging (LIDAR), radar, infrared beam, or other wave-reflection techniques.

In some implementations, a triangulation technique for determining the position of a fluid leak uses a common object associated to the fluid leak that appears in two or more photographic images that were taken from different locations and/or angles to determine the object location. For example, the triangulation technique can be based on principles of the range finding camera that uses the looming equation. The looming equation assumes a constant focal length f and the size of a projection of an object onto the focal plane depends on the distance between the object and the camera. The object's height can be automatically determined from the image. By moving the vehicle with the digital camera a known distance and taking another picture, the object's height is modified and it can be determined from the second image. The variation in height and length of camera's displacement (e.g., vehicle's displacement) can be used to automatically determine the distance from the camera to the object.

In some implementations, the position of the fluid leak can be determined by using an image overlay technique that immediately uses the images of the actual physical surroundings that are matched to a map database. For example, the captured images can be used to create composite two- or three-dimensionally rendered map that indicates amounts of the fluid at a plurality of distances from retrieved geographical locations (e.g., geographical locations indicated by GPS). The composite two- or three-dimensionally rendered map can be determined based on the vehicle location data (e.g., GPS), the orientation of the camera (e.g., pointing northwest), and a distance estimate determined from the image(s) (e.g., processing the image using a computer-vision program, such as OpenCV®). For example, the GPS coordinates of vehicle at a particular location are recorded, the orientation of the camera is determined (e.g., pointing northwest), and distance from an object that is identified as being associated to the fluid leak is calculated (e.g., 50 m). Within the context example, the location of the fluid leak is determined to be given by the GPS coordinates of vehicle, to which the calculated distance (e.g., 50 meters) is added in the identified orientation of the camera (e.g., northwest). For example, the coordinates of the fluid leak can be provided as 50 m, 330° NW of the vehicle GPS coordinates.

The extraction of fluid leak volume can include determining an accurate position of multiple points defining a three-dimensional boundary of the fluid leak, shape recognition techniques, and volume rendering techniques. The quantity of the fluid leak can be determined based on the volume of the fluid leak and the concentration of the fluid, as indicated by the vectors of the hyperspectral images. In some implementations, the quantity of the fluid leak and one or more additional information (e.g., surface of affected area, existence of affected vegetation, number of people exposed to the fluid leak, and duration of exposure of people to the fluid leak) can be used to determine a severity of the accident. The severity level can include a severe fluid leak, a moderate fluid leak and a minor fluid leak. For example, if a digital image indicates the presence of people in the proximity of the fluid leak and the hyperspectral images indicate a large volume of fluid, it can be determined that a severe fluid leak with high risk has occurred. As another example, if the digital images do not indicate the presence of people nor affected vegetation in the proximity of the fluid leak and the hyperspectral images indicate a medium volume of fluid, it can be determined that a moderate fluid leak with moderate risk exists. As another example, if the digital images do not indicate the presence of people nor affected vegetation in the proximity of the fluid leak and the hyperspectral images indicate a small volume of fluid (e.g., near a pipeline), it can be determined that a mild fluid leak with minor risk exists. In some implementations, the mild fluid leaks are further processed to differentiate between false positive results (e.g. random fluid spills that are improbable to reoccur) and true minor fluid leaks. For example, the distance between the fluid leak and a potential source of the fluid leak (e.g., a gas pipeline) is determined and corrected for wind-induced displacement. In some implementations, if the distance between the fluid leak and the potential source is smaller than a threshold (e.g., 1 meter), the fluid leak is determined as being a true mild fluid leak.

Fluid leak information is provided (410). For example, fluid leak information can be displayed on a GUI, as described with reference to FIG. 3. The fluid leak information can include severity of the fluid leak, location of the fluid leak, quantity of the fluid leak, type of fluid within the fluid leak, existence of affected people and vegetation, potential immediate risks, future risks, and/or types and quantities of tools and materials that need to be used for neutralize the fluid leak and its effects. In some implementations, in response to determining that a fluid leak has occurred, information related to the fluid leak is provided to one or more entities based on a set of rules. The entities can include entities that can coordinate and/or perform remedial actions (e.g., repair an equipment that generates the fluid leak, clean the fluid spill, and neutralize the impact on the affected area) and/or provide medical assistance to any persons who could have been affected by the fluid leak.

The set of rules can be associated with the severity of the fluid leak and the type of fluid leak. For example, if the fluid leak is determined to be mild or moderate, fluid leak information, including location of fluid leak, fluid type, and estimated quantity of fluid, is sent to an entity that can be associated to the fluid leak (e.g., a provider of the identified fluid type for the identified location of the fluid leak) and/or an entity configured to dispatch service vehicles to repair the leaking equipment and to prevent future fluid leaks. As another example, if the fluid leak is determined to be severe a portion or all information associated with the fluid leak is sent to an entity that can be associated to the fluid leak (e.g., a provider of the identified fluid type for the identified location of the fluid leak), an entity configured to dispatch service vehicles to repair the leaking equipment and to prevent future fluid leaks, an entity configured to dispatch emergency responders who can provide medical assistance, and/or fire department if the if the concentration of the leaking fluid is identified near or above an explosive level threshold.

In some implementations, the fluid leak information is transmitted as an alert to a remote device in real time (e.g., substantially immediately after the data processing is completed and the fluid leak characteristics were determined). The alert can include at least one of a vibrating alert, an audible alert, and a visual alert. In some implementations, one or more characteristics of the visual alert (e.g., content of data, font sizes and/or background color) can depend on the severity of the fluid leak. In some implementations, the example process 400 includes receiving a response from an entity, such as a confirmation that remedial actions have been performed to neutralize the fluid leak. In some implementations, the example process 400 can be repeated multiple times using a single detection vehicle and/or can be performed by multiple detection vehicles in parallel or at separate times. For example, the output data of the process 400 indicating multiple fluid leak locations can be integrated by a pipeline operator's maintenance management software to automatically set a follow-up inspection and/or a leak repair plan. The plan can prioritize the repair of fluid leaks based on one or more parameters associated to the fluid leak. The parameters associated to the fluid leak can include the size of fluid leak, availability of repair team personnel, federal and state rules, associated risks, and/or proximity to high consequence areas (e.g., school).

Implementations and all of the functional operations described in this specification can be realized in digital electronic circuitry, or in computer software, firmware, or hardware, including the structures disclosed in this specification and their structural equivalents, or in combinations of one or more of them. Implementations can be realized as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus can include, in addition to hardware, code that creates an execution environment for the computer program in question (e.g., code that constitutes processor firmware, a protocol stack, a database management system, an operating system, or a combination of one or more of them). A propagated signal is an artificially generated signal, e.g., a machine-generated electrical, optical, or electromagnetic signal that is generated to encode information for transmission to suitable receiver apparatus.

A computer program (also known as a program, software, software application, script, or code) can be written in any appropriate form of programming language, including compiled or interpreted languages, and it can be deployed in any appropriate form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations can be realized on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any appropriate form of sensory feedback, e.g., visual feedback, auditory feedback, or tactile feedback; and input from the user can be received in any appropriate form, including acoustic, speech, or tactile input.

Implementations can be realized in a computing system that includes a back end component, e.g., as a data server, or that includes a middleware component, e.g., an application server, or that includes a front end component, e.g., a client computer having a graphical user interface or a Web browser through which a user can interact with an implementation, or any appropriate combination of one or more such back end, middleware, or front end components. The components of the system can be interconnected by any appropriate form or medium of digital data communication (e.g., a communication network). Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what can be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications can be made without departing from the spirit and scope of the disclosure. For example, various forms of the flows shown above can be used, with steps re-ordered, added, or removed. Accordingly, other implementations are within the scope of the following claims.

What is claimed is:

1. A computer-implemented method for detecting a fluid leak, the method being executed by one or more processors and comprising:
    capturing, by one or more digital cameras, at least one image, the one or more digital cameras being included in an imaging system attached to a vehicle moving between geographical locations, and the at least one image corresponding to a geographical location;
    generating, by one or more fluid detectors, spectral data indicative of at least one fluid at the geographical location, the one or more fluid detectors being dynamically aligned with the one or more digital cameras, wherein the one or more fluid detectors modify a fluid detection orientation based on a modification of an imaging orientation of the one or more digital cameras;
    receiving, by the one or more processors, from the one or more digital cameras the at least one image, and from the one or more fluid detectors, the spectral data of the fluid at the geographical location; and
    providing, by the one or more processors, an output signal based on the at least one image and the spectral data, the output signal indicating a fluid leak.

2. The method of claim 1, wherein the output signal comprises a location of the fluid leak.

3. The method of claim 2, wherein the location of the fluid leak comprises the geographical location, a distance between the vehicle and the fluid leak determined based on at least a first portion of the at least one image and at least a second portion of the spectral data, and an orientation.

4. The method of claim 1, wherein the output signal indicates an amount of the fluid relative to the geographical location.

5. The method of claim 4, further comprising comparing the amount of the fluid to a set amount.

6. The method of claim 1, wherein the at least one image and the spectral data are concurrently captured at the geographical location.

7. The method of claim 1, wherein the one or more digital cameras and the one or more fluid detectors are rotatable about one or more of a vertical axis and a horizontal axis.

8. The method of claim 1, wherein the geographical location comprises geographical coordinates that are determined by at least one of an accelerometer, a gyroscope, a magnetometer, and a global positioning system sensor.

9. The method of claim 1, wherein the fluid comprises a gas.

10. The method of claim 1, wherein the fluid comprises at least one of hydrocarbons and organic compounds.

11. The method of claim 10, wherein the hydrocarbon comprises at least one of a carbon dioxide, a methane, and an ethylene.

12. The method of claim 1, wherein the spectral data corresponds to an optical beam that comprises one or more optical wavelengths.

13. The method of claim 1, wherein the at least one image and the spectral data are transmitted from the vehicle to a remote device configured to generate the output signal.

14. One or more non-transitory computer-readable storage media coupled to one or more processors and having instructions stored thereon which, when executed by the one or more processors, cause the one or more processors to perform operations for detecting a fluid leak, the operations comprising:
    sending a first signal to one or more digital cameras to capture at least one image, the one or more digital camera being included in an imaging system attached to a vehicle moving between geographical locations, and the at least one image corresponding to a geographical location;
    sending a second signal to one or more fluid detectors to generate spectral data indicative of at least one fluid at the geographical location, the one or more fluid detectors being dynamically aligned with the one or more digital cameras, wherein the one or more fluid detectors modify a fluid detection orientation based on a modification of an imaging orientation of the one or more digital cameras;
    receiving from the one or more digital cameras the at least one image, and from the one or more fluid detectors the spectral data of the fluid at the geographical location; and
    providing an output signal based on the at least one image and the spectral data, the output signal indicating a fluid leak.

15. A system, comprising:
    one or more digital cameras configured to capture at least one image, the one or more digital camera being included in an imaging system attached to a vehicle moving between geographical locations, and the at least one image corresponding to a geographical location;
    one or more fluid detectors configured to generate spectral data indicative of at least one fluid at the geographical location, the one or more fluid detectors being dynamically aligned with the one or more digital cameras, wherein the one or more fluid detectors modify a fluid detection orientation based on a modification of an imaging orientation of the one or more digital cameras;
    one or more processors; and
    a computer-readable storage device coupled to the one or more processors and having instructions stored thereon which, when executed by the one or more processors, cause the one or more processors to perform operations for detecting a fluid leak, the operations comprising:
    receiving from the one or more digital cameras the at least one image, and from the one or more fluid detectors the spectral data of the fluid at the geographical location; and
    providing an output signal based on the at least one image and the spectral data, the output signal indicating a fluid leak.

16. The system of claim 15, wherein the one or more fluid detectors comprise a hyperspectral camera.

17. The system of claim 15, wherein the one or more processors and the computer-readable storage device are at a second geographical location that is remote from the vehicle.

18. The system of claim 15, wherein the one or more digital cameras and the one or more fluid detectors are rotatable about one or more of a vertical axis and a horizontal axis.

* * * * *